(12) United States Patent
Lin et al.

(10) Patent No.: US 8,569,249 B2
(45) Date of Patent: Oct. 29, 2013

(54) METHOD FOR INHIBITING ACTIVATION OF MACROPHAGES

(75) Inventors: Wen-Chuan Lin, Taichung (TW); Jin-Bin Wu, Taipei (TW); Hui-Ya Ho, Taichung (TW); Hung-Bo Hsiao, Taichung (TW)

(73) Assignee: China Medical University, Taichung (TW)

(*) Notice: Subject to any disclaimer, the term of this patent is extended or adjusted under 35 U.S.C. 154(b) by 230 days.

(21) Appl. No.: 13/161,369

(22) Filed: Jun. 15, 2011

(65) Prior Publication Data

US 2012/0238513 A1    Sep. 20, 2012

(30) Foreign Application Priority Data

Mar. 14, 2011 (TW) .............................. 100108508 A

(51) Int. Cl.
- *A01N 43/04* (2006.01)
- *A61K 31/70* (2006.01)
- *C07H 15/00* (2006.01)
- *C07H 17/00* (2006.01)

(52) U.S. Cl.
USPC ................................................ 514/32; 536/8

(58) Field of Classification Search
None
See application file for complete search history.

(56) References Cited

FOREIGN PATENT DOCUMENTS

WO    03/031430 A2    4/2003

OTHER PUBLICATIONS

Grom et al., Macrophage activation syndrome: advances towards understanding pathogenesis, Current Opinion in Rheumatology, 2010. 22: 561-566.

Deryugina et at, Matrix metalloproteinases and tumor metastasis, Cancer Metastasis Rev., 2006, 25: 9-34.

Neuman RE., Logan MA. The determination of hydroxyproline. J. Biol. Chem. 1950; 184: 299-306.

Su, G, L., 2002. Lipopolysaccharides in liver injury: molecular mechanisms of Kupffer cell activation. Am. J. Physiol. 283, G256-G265.

Thorbecke et al., Modulation by cytokines of induction of oral tolerance to type II collagen. Arthritis Rheum., 1999, 42 (1): 110-8.

Ong, D., "The Physiological Activities of Tea Catechins", Master's Dissertation, National Taiwan Ocean University, Jun. 2005.

*Primary Examiner* — Lawrence E Crane

(74) *Attorney, Agent, or Firm* — Ping Wang; Andrews Kurth LLP

(57) ABSTRACT

Provided is a method for inhibiting the activation of macrophages in a subject, comprising administrating to the subject an effective amount of an active component selected from the group consisting of a compound of formula (I), a pharmaceutically acceptable salt of the compound, and a pharmaceutically acceptable ester of the compound, and combinations thereof:

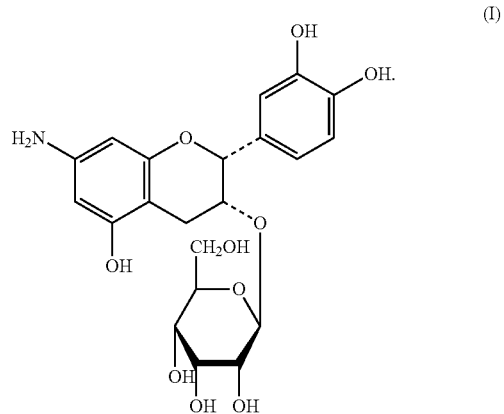

9 Claims, 12 Drawing Sheets

SEQUENCE LISTING

<160> NUMBER OF SEQ ID NOS: 12

<210> SEQ ID NO 1
<211> LENGTH: 21
<212> TYPE: DNA
<213> ORGANISM: Artificial Sequence
<220> FEATURE:

```
<223> OTHER INFORMATION: forward primer for iNOS

<400> SEQUENCE: 1
cagctgggct gtacaaacct t                                          21

<210> SEQ ID NO 2
<211> LENGTH: 21
<212> TYPE: DNA
<213> ORGANISM: Artificial Sequence
<220> FEATURE:
<223> OTHER INFORMATION: reverse primer for iNOS

<400> SEQUENCE: 2
cattggaagt gaagcgtttc g                                          21

<210> SEQ ID NO 3
<211> LENGTH: 27
<212> TYPE: DNA
<213> ORGANISM: Artificial Sequence
<220> FEATURE:
<223> OTHER INFORMATION: forward primer for GAPDH

<400> SEQUENCE: 3
cttcattgac ctcaactaca tggtcta                                    27

<210> SEQ ID NO 4
<211> LENGTH: 23
<212> TYPE: DNA
<213> ORGANISM: Artificial Sequence
<220> FEATURE:
<223> OTHER INFORMATION: reverse primer for GAPDH

<400> SEQUENCE: 4
gatgacaagc ttcccattct cag                                        23

<210> SEQ ID NO 5
<211> LENGTH: 20
<212> TYPE: DNA
<213> ORGANISM: Artificial Sequence
<220> FEATURE:
<223> OTHER INFORMATION: reverse primer for IL-1.beta.

<400> SEQUENCE: 5
tggtttctct tcccaagacc                                            20

<210> SEQ ID NO 6
<211> LENGTH: 20
<212> TYPE: DNA
<213> ORGANISM: Artificial Sequence
<220> FEATURE:
<223> OTHER INFORMATION: forward primer for IL-1.beta.

<400> SEQUENCE: 6
ttcaagggga cattaggcag                                            20

<210> SEQ ID NO 7
<211> LENGTH: 20
<212> TYPE: DNA
<213> ORGANISM: Artificial Sequence
<220> FEATURE:
<223> OTHER INFORMATION: reverse primer for IL-1.beta.
```

```
<400> SEQUENCE: 7
tgtgctggtg cttcattcat                                              20

<210> SEQ ID NO 8
<211> LENGTH: 19
<212> TYPE: DNA
<213> ORGANISM: Artificial Sequence
<220> FEATURE:
<223> OTHER INFORMATION: reverse primer for IL-1.beta.

<400> SEQUENCE: 8
agggacagaa cctgcctgg                                               19

<210> SEQ ID NO 9
<211> LENGTH: 18
<212> TYPE: DNA
<213> ORGANISM: Artificial Sequence
<220> FEATURE:
<223> OTHER INFORMATION: forward primer for MMP-9

<400> SEQUENCE: 9
ggtctaggcc cagaggta                                                18

<210> SEQ ID NO 10
<211> LENGTH: 18
<212> TYPE: DNA
<213> ORGANISM: Artificial Sequence
<220> FEATURE:
<223> OTHER INFORMATION: reverse primer for MMP-9

<400> SEQUENCE: 10
ggtcgtaggt cacgtagc                                                18

<210> SEQ ID NO 11
<211> LENGTH: 32
<212> TYPE: DNA
<213> ORGANISM: Artificial Sequence
<220> FEATURE:
<223> OTHER INFORMATION: sequence for electrophoretic mobility shift
      assay of NF-.kappa.B

<400> SEQUENCE: 11
tcgaccaact ggggactctc cctttgggaa ca                                32

<210> SEQ ID NO 12
<211> LENGTH: 32
<212> TYPE: DNA
<213> ORGANISM: Artificial Sequence
<220> FEATURE:
<223> OTHER INFORMATION: sequence for electrophoretic mobility shift
      assay of NF-.kappa.B

<400> SEQUENCE: 12
tcgatgttcc caagggaga gtccccagtt gg                                 32
```

METHOD FOR INHIBITING ACTIVATION OF MACROPHAGES

CROSS-REFERENCES TO RELATED APPLICATIONS

This application claims the benefit of Taiwan Patent Application No. 100108508, filed on Mar. 14, 2011, in the Taiwan Intellectual Property Office, the disclosure of which is incorporated herein in its entirety by reference.

FIELD

The present invention relates to the use of (−)-Epicatechin-3-O-β-D-allopyranoside in the inhibition of the activation of macrophages, especially in curing macrophage activation syndrome (MAS), curing or inhibiting inflammation, and inhibiting the expression of matrix metalloproteinase-9 (MMP-9).

BACKGROUND

Macrophages are white blood cells formed by the differentiation of monocytes in tissue. Macrophages participate in innate immunity by phagocytosing pathogens or cellular debris, or help initiate adaptive immunity by stimulating other immune cells, such as lymphocytes, to fight against pathogens.

A majority of macrophages gather in the tissue or organs where pathogen invasion is likely to occur. Macrophages have different names based on their locations in the body. For example, macrophages located in the liver are called Kupffer cells; macrophages in the spleen are called sinusoidal lining cells; macrophages in the bone are called osteoclasts; and macrophages in the kidney are called mesangial cells.

Even though macrophages help the animal body fight pathogen infections, over-activation (or excessively high activity) of macrophages may cause the disorder of immune system in the body, resulting in various inflammatory diseases (such as arthritis, hepatitis, or splenitis) and even the generation of cancers (such as sarcomatous cancer, prostate cancer, glioblastoma cancer, melanoma cancer, lung cancer, pancreatic cancer, or ovarian cancer). For example, this over-activation of macrophages may result in macrophage activation syndrome (MAS).

Considering that the over-activation of macrophages may cause various diseases described above, a medicine or a method is needed for effectively inhibiting the activation of macrophages to cure the diseases derived from the over-activation of macrophages.

The present invention is a result of the study conducted for the above demand. The inventors of the present invention found that (−)-Epicatechin-3-O-β-D-allopyranoside can effectively inhibit the activation of macrophages, and thus, it can be used for curing the diseases related to the over-activation of macrophages.

SUMMARY

The primary objective of this invention is to provide a method for inhibiting the activation of macrophages in a subject, comprising administrating to the subject an effective amount of an active component selected from the group consisting of a compound of formula (I), a pharmaceutically acceptable salt of the compound, a pharmaceutically acceptable ester of the compound, and combinations thereof:

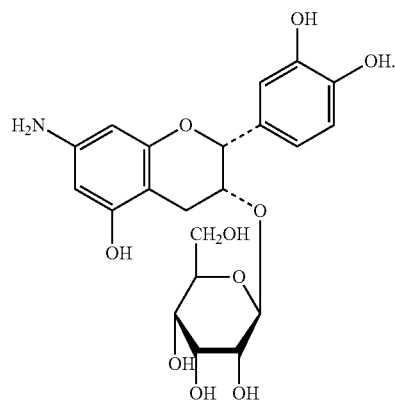

Another objective of this invention is to provide a pharmaceutical composition for inhibiting the activation of macrophages, which comprises an effective amount of the aforesaid active component and a pharmaceutically acceptable carrier.

The detailed technology and preferred embodiments implemented for the subject invention are described in the following paragraphs accompanying the appended drawings for people skilled in this field to well appreciate the features of the claimed invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF THE PREFERRED EMBODIMENT

Figure 1:
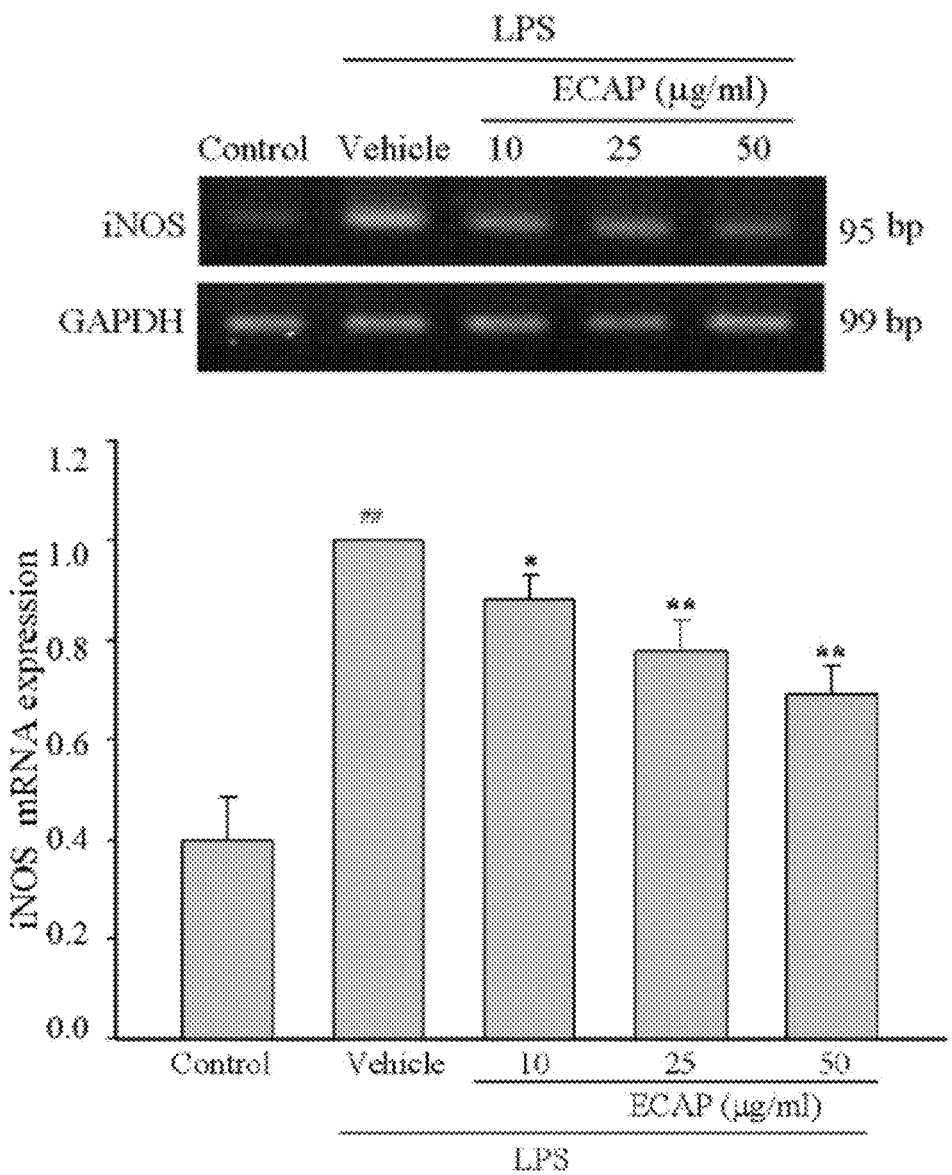
FIG. 1 is an electrophoresis picture and a statistic column diagram showing the inhibition of ECAP on the mRNA expression of inducible nitric oxide synthase (iNOS) in macrophages.

Unless otherwise stated herein, the terms "a (an)", "the" or the like used in this specification (especially in the Claims hereinafter) shall be understood to encompass both the singular form and the plural form.

Macrophages can be activated by the stimulation of various inflammatory factors, including physical factors (such as temperature and UV), chemical factors (such as acid and alkali), mechanical factors (such as extrusion and collision), biological factors (such as lipopolysaccharide (LPS), viral infection, and toxins), or autoimmune diseases, etc. An inflammatory reaction may stimulate the immune system to produce a large amount of cytokines to promote the proliferation and activation of macrophages. Macrophages can further produce free radicals, such as nitric oxide, to perform subsequent immune responses, such as killing viruses, bacteria or tumor cells, etc. However, as described above, if the inflammatory reaction continues for a long period, it may cause the over-activation of macrophages and result in various related diseases. The inventors of the present invention found that (+Epicatechin-3-O-β-D-allopyranoside (hereinafter referred to as "ECAP") can effectively inhibit the activation of macrophages, and thus, it can be used for curing the diseases related to the over-activation of macrophages.

Therefore, the present invention provides a method for inhibiting the activation of macrophages in a subject, comprising administrating to the subject an effective amount of an active component selected from the group consisting of a compound of formula (I), a pharmaceutically acceptable salt of the compound, a pharmaceutically acceptable ester of the compound, and combinations thereof:

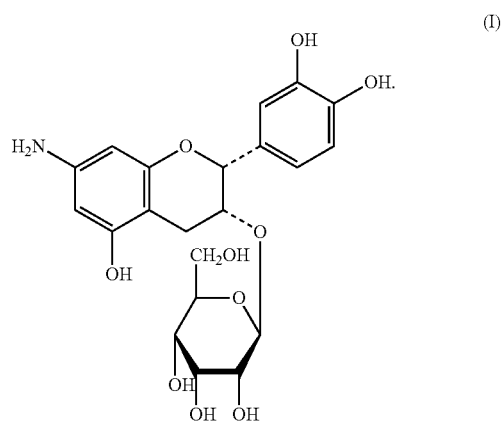

Preferably, the active component is the compound of formula (I).

The compound of formula (I) is ECAP, which is from *Davallia formosana*. Due to the effect of ECAP to effectively inhibit the activation of macrophages, it can be used for curing macrophage activation syndrome, and curing or inhibiting inflammation or inflammation-related diseases. Macrophage activation syndrome (MAS) is the major cause for the morbidity and mortality of pediatric rheumatology, and it also highly correlates with systemic juvenile idiopathic arthritis (SJIA) and lupus erythematosus. Patients with macrophage activation syndrome may have symptoms of fever, hepatosplenomegaly, lymph node swelling, severe reduction of haemacyte, coagulopathy, liver dysfunction, etc. The mechanism and symptoms related to macrophage activation syndrome can be seen in Grom et al., Macrophage activation syndrome: advances towards understanding pathogenesis, Current Opinion in Rheumatology, 2010. 22: 561-566, which is entirely incorporated hereinto by reference.

When an inflammatory reaction occurs in the liver and continues for a long time to cause the macrophages in the liver (i.e., Kupffer cells) to over-activate, chronic hepatitis may arise. About twenty percent of patients with chronic hepatitis suffer from liver fibrosis or liver cirrhosis, or even die. In one embodiment, the method of the present invention can effectively inhibit the activation of macrophages in the liver, and further inhibit hepatitis. Therefore, the method of the present invention can be used for curing hepatitis, including chronic hepatitis, liver fibrosis or liver cirrhosis.

In joint cavities, severe and persistent inflammatory reaction may cause the over-activation of macrophages and result in arthritis. Arthritis generally refers to the diseases related to abnormal joint inflammation. Based on the clinical symptoms, arthritis can be classified into various types, such as osteoarthritis, rheumatoid arthritis, sepsis arthritis, etc. In one embodiment, due to the effect of inhibiting the activation of macrophages in bones (or osteoclasts) and further inhibiting arthritis of the method of the present invention, it can be used to cure arthritis, especially rheumatoid arthritis.

In another aspect, inflammatory reaction can stimulate macrophages to release matrix metalloproteinase-9 (MMP-9). Matrix metalloproteinase-9 belongs to the matrix metalloproteinase family, has the ability to cleave and decompose collagen and extracellular matrix, and is related to the occurrence of various diseases. For example, severe and persistent inflammatory reaction in a joint may induce the differentiation of macrophages into osteoclasts. Osteoclasts can further release matrix metalloproteinase-9, which can decompose the bone matrix and cause bone damage. In addition, it is known that matrix metalloproteinase-9 involves the proliferation, migration and invasion of tumor cells, and it can help the spread of tumor cells by regulating angiogenesis and decomposing extracellular matrix. Matrix metalloproteinase-9 also relates to carcinoma, such as osteosarcoma, sarcoma, lymphoma, prostate carcinoma, glioblastoma, melanoma, lung carcinoma, pancreatic carcinoma, ovarian carcinoma, breast carcinoma, etc. The information regarding the relation between matrix metalloproteinase-9 and tumor formation can be seen in Deryugina et al., Matrix metalloproteinases and tumor metastasis, *Cancer Metastasis Rev.*, 2006, 25: 9-34, which is entirely incorporated hereinto by reference.

As shown in the following examples, the method of the present invention can effectively inhibit the expression of matrix metalloproteinase-9, and thus, it can be used for curing or inhibiting the diseases relevant to matrix metalloproteinase-9. For example, the method can be used for inhibiting the proliferation, migration and/or invasion of tumor cells, and curing cancer. The method of the present invention especially can be used to inhibit the proliferation, migration and/or invasion of carcinoma cells, such as osteosarcoma cells, sarcoma cells, lymphoma cells, prostate carcinoma cells, glioblastoma cells, melanoma cells, lung carcinoma cells, pancreatic carcinoma cells, ovarian carcinoma cells, breast carcinoma cells, etc.

In the method of the present invention, the aforesaid active component can be administrated as a medicament. Therefore, the present invention also provides a pharmaceutical composition for inhibiting the activation of macrophages. The pharmaceutical composition comprises a pharmaceutically acceptable carrier and an effective amount of the active component.

The pharmaceutical composition of the present invention can be used in both the veterinary and human medicine, and it can be any suitable form and can be applied by any suitable manner without particular limits. For example, but not limited thereby, the pharmaceutical composition can be applied by oral administration, subcutaneous injection, intravenous injection, intra-articular injection, etc. Depending on the form and purpose of the pharmaceutical composition of the present invention, the pharmaceutical composition may comprise a pharmaceutically acceptable carrier.

In terms of the manufacturing of a medicament suitable for oral administration, the pharmaceutical composition of the present invention can comprise a pharmaceutically acceptable carrier which has no adverse influence on the activity of ECAP, such as solvents, oily solvents, thinners, stabilizers, absorption delaying agents, disintegrants, emulsifiers, antioxidants, binders, lubricants, moisture absorbents, etc. The pharmaceutical composition can be prepared in a form suitable for oral administration by any suitable approach, such as a tablet, a capsule, a granule, powder, a fluid extract, a solution, syrup, a suspension, an emulsion, a tincture, etc.

As for a medicament suitable for subcutaneous, intravenous, or intra-articular injection, the pharmaceutical composition of the present invention can comprise one or more components, such as an isotonic solution, a saline buffer solution (such as a phosphate buffer solution or a citrate buffer solution), a solubilizer, an emulsifier, other carriers, etc, to produce an intravenous injection, an emulsion intravenous injection, a powder injection, a suspension injection, a powder-suspension injection, etc.

Optionally, in addition to the above adjuvants, other additives, such as a flavoring agent, a toner, a coloring agent, etc., can be added to the pharmaceutical composition of the present invention to enhance the taste and visual appeal of the composition. A suitable amount of a preservative, a conservative, an antiseptic, an anti-fungus reagent, and so on, also can be added to improve the storability of the resultant medicament.

The pharmaceutical composition may optionally combine one or more other active components to enhance the effect of the medicament or increase the flexibility for the formulation. For example, one or more active components, such as steroidal anti-inflammation drugs, non-steroidal anti-inflammation drugs, glucosamine, anti-cancer drugs, other active components, etc, can be incorporated into the pharmaceutical composition of the present invention, as long as the other active components have no adverse effect on ECAP.

Depending on the requirements of the subject, the pharmaceutical composition of the present invention can be applied with various administration frequencies, such as once a day, several times a day, or once for days, etc. For example, when applied to the human body for treating rheumatoid arthritis, the dose of the pharmaceutical composition is about 50 mg/kg-body weight to about 300 mg/kg-body weight per day, based on the compound of formula (I), wherein the unit "mg/kg-body weight" means the dosage required per kg-body weight. However, for patients with acute conditions (e.g., patients with gout), the dosage can be increased to several times or several tens of times, depending on practical requirements.

The detailed technology and preferred embodiments implemented for the present invention are described in the following paragraphs; however, the scope of the present invention is not limited thereby.

EXAMPLE

Preparation Example

Preparation of ECAP (the Compound of Formula (I))

(1) Preparation of an Extract of *Davallia formosana*

The roots and stems of *Davallia formosana* were extracted twice with 75% by volume of ethanol, and the obtained extract was placed under reduced pressure at 50° C. to evaporate the solvent. The yield of the ethanol extract of *Davallia formosana* was 9.5 wt %. The dosage of the ethanol extract of *Davallia formosana* used in the present experiments was based on the dry weight of the extract. The ethanol extract was suspended in water and partitioned by n-butanol, and the n-butanol fraction was concentrated. The yield of the n-butanol fraction obtained from the ethanol extract was 20.2 wt %.

(2) Purification of ECAP

The n-butanol fraction (10 g) was introduced into an HP-20 column (Diaion, NIPPO N RESSUI Company, Japan) and eluted with water followed by methanol. Eight fractions were obtained (Fractions 1 to 8). Fraction 6 (230 mg) was purified by a preparative high performance liquid chromatograph (HPLC) to obtain a pure compound (136 mg). The operation conditions for the preparative HPLC (Shimadzu LC-8A, Kyoto, Japan) were as follows: the mobile phase, methanol-water (9:1); the column, 5C18-MS-II (Cosmosil Nacalai Tesque Company, Japan); the internal diameter of the column, 10 mm; the length of the column: 250 mm.

The pure compound was analyzed by NMR ($^1$H, $^{13}$C; Bruker ADVANCE DPX-200, Germany), and the compound was identified as (−)-Epicatechin-3-O-β-D-allopyranoside (ECAP, the compound of formula (I)). The result of the $^{13}$C and $^1$H NMR spectrum (200 MHz, CDCl$_3$) of ECAP is shown in Table 1.

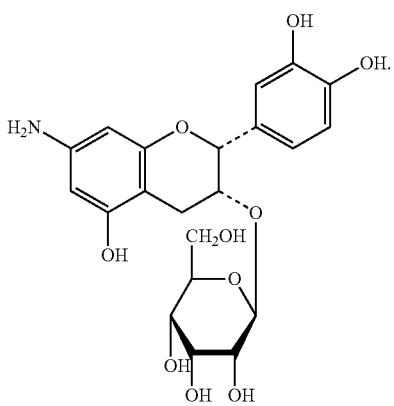

(I)

TABLE 1

| C | | H | |
|---|---|---|---|
| C-2 | 79.19 | 2-H | 5.05 (d, J = 2.2 Hz) |
| C-3 | 73.40 | 3-H | 4.43 (m) |
| C-4 | 24.75 | 4-2H | 2.74, 2.72 |
| C-5 | 157.85 | | |
| C-6 | 96.43 | 6-H | 5.86 (d, J = 2.4 Hz) |
| C-7 | 157.85 | | |
| C-8 | 95.68 | 8-H | 5.90 (d, J = 2.4 Hz) |
| C-9 | 157.13 | | |
| C-10 | 100.21 | | |
| C-1' | 131.67 | | |
| C-2' | 115.57 | 2'-H | 7.02 (d, J = 2.4 Hz) |
| C-3' | 145.50 | | |
| C-4' | 145.72 | | |
| C-5' | 116.29 | 5'-H | 6.66 (d, J = 8.2 Hz) |
| C-6' | 120.34 | 6'-H | 6.78 (dd, J = 1.8, 8.2 Hz) |
| Allosyl | | Allosyl | |
| C-1" | 100.41 | 1"-H | |
| C-2" | 72.28 | (2"-6"-H) | 4.74 (d, J = 8 Hz) |
| C-3" | 72.91 | (5H) | 3.22-3.99 |
| C-4" | 68.96 | | |
| C-5" | 75.33 | | |
| C-6" | 63.26 | | |

Example 1

Inhibition Test of the Inflammatory Reaction of Macrophages

Macrophages play an important role in the inflammatory reaction, and they can mediate various immune pathological responses. After being activated, macrophages can generate various inflammatory mediators, such as nitric oxide (NO). Because macrophages can be activated by the stimulation of various inflammatory substances (such as lipopolysaccharide (LPS)), lipopolysaccharide was used in the following experiments to activate macrophages to release nitric oxide. With this model, the anti-inflammation effect of ECAP was studied.

Experiment A

Measurement of the Content of Nitric Oxide

ECAP with different concentrations (0, 10, 25, and 50 μg/ml) was added into a 96-well culture dish (containing Dulbecco's modified eagle's culture medium (DMEM), 10 wt % heat inactivated FBS, 100 U/ml penicillin, and 100 μg/ml streptomycin) comprising RAW 264.7 macrophages. The cells were cultured for 1 hour, and then 1 μM lipopolysaccharide was added into the culture dish. After the cells were cultured for 24 hours, the supernatant was collected, and the content of nitric oxide was determined by a Griess reagent. The result is shown in Table 2. In addition, the survival rate of the macrophages was determined by MTS (3-(4,5-di-methylthiazol-2-yl)-5-(3-carboxymethoxyphenyl)-2-(4-sulfophenyl)-2H-tetrazolium) (Promega, Madison, Wis., USA). The result shows that the survival rate of RAW 264.7 macrophages was not affected by ECAP or the combination of ECAP with lipopolysaccharide.

TABLE 2

| Group | ECAP concentration (μg/ml) | NO (μM) |
|---|---|---|
| control | — | 6.7 ± 0.9 |
| LPS + vehicle | 0 | 57.2 ± 3.4### |
| LPS + ECAP | 10 | 39.6 ± 3.4***(30.8%) |
| | 25 | 33.5 ± 2.7***(41.4%) |
| | 50 | 18.0 ± 0.8***(68.5%) |

Values are means ± SD (n = 3).
P < 0.001 as compared with the control group.
***P < 0.001 as compared with the LPS + vehicle group.

Experiment B

Determination of the Gene Expression of Inducible Nitric Oxide Synthase (iNOS)

RAW 264.7 macrophages were incubated in a cell culture dish with a diameter of 6 cm ($1 \times 10^6$/dish), and ECAP with different concentrations (0, 10, 25, and 50 μg/ml) was added into the cell culture dish, and the cells were cultured for 1 hour, and then lipopolysaccharide (1 μg/ml) was added into the cell culture dish. After the cells were cultured for 24 hours, the cells were collected and the mRNAs thereof were extracted. The gene expression of inducible nitric oxide synthase (iNOS) was analyzed by RT-PCR, and glyceraldehyde-3-phosphate dehydrogenase (GAPDH) gene was used as an internal control. The primers used in this experiment are shown in Table 3. The results of this experiment are shown in FIG. 1 and Table 4.

TABLE 3

| primer | | sequence | length | Tm |
|---|---|---|---|---|
| mouse iNOS | F | CAGCTGGGCTGTACAAACCTT (SEQ ID NO. 1) | 95 b.p. | 53° C. |
| | R | CATTGGAAGTGAAGCGTTTCG (SEQ ID NO. 2) | | |
| GAPDH | F | CTTCATTGACCTCAACTACATGGTCTA (SEQ ID NO. 3) | 99 b.p. | 55° C. |
| | R | GATGACAAGCTTCCCATTCTCAG (SEQ ID NO. 4) | | |

TABLE 4

| Group | Relative content (iNOS) |
|---|---|
| control | 0.405 ± 0.085## |
| vehicle | 1.000 ± 0.000## |

TABLE 4-continued

| Group | Relative content (iNOS) |
|---|---|
| ECAP 10 μg/ml | 0.880 ± 0.055* |
| ECAP 50 μg/ml | 0.789 ± 0.056** |
| ECAP 100 μg/ml | 0.694 ± 0.065** |

Values are means ± SD (n = 3).
P < 0.01 as compared with the control group.
*P < 0.05 as compared with the vehicle group.
**P < 0.01 as compared with the vehicle group.

Experiment C

Determination of the Protein Expression of iNOS

Figure 2:
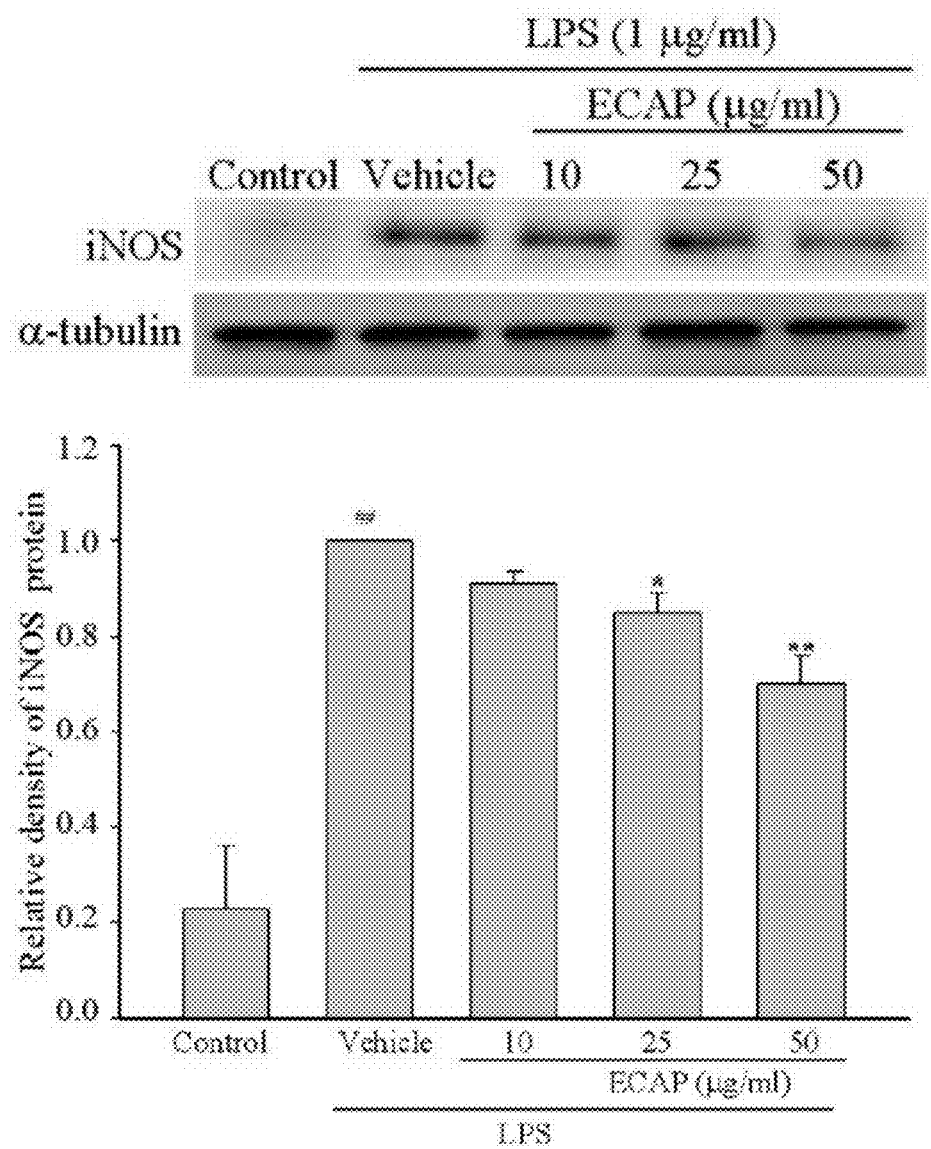
FIG. 2 is an electrophoresis picture and a statistic column diagram showing the inhibition of ECAP on the protein expression of inducible nitric oxide synthase in macrophages.

RAW 264.7 macrophages were cultured in a cell culture dish with a diameter of 6 cm to a cell density of $1 \times 10^6$ cells/dish. Different concentrations (0, 10, 25, and 50 μg/ml) of ECAP were added into the cell culture dish, and the cells were cultured for 1 hour, and then lipopolysaccharide (1 μg/ml) was added into the cell culture dish. After being cultured for 24 hours, the cells were collected, and the proteins in the cytoplasm were extracted. The protein expression of inducible nitric oxide synthase (iNOS) was analyzed by Western Blot. The antibody used in this experiment was anti-rabbit iNOS (Ab cam Cambridge, USA). The results are shown in FIG. 2 and Table 5.

TABLE 5

| Group | Relative content (iNOS) |
|---|---|
| control | 0.230 ± 0.132 |
| vehicle | 1.000 ± 0.000## |
| ECAP 10 μg/ml | 0.913 ± 0.026 |
| ECAP 50 μg/ml | 0.847 ± 0.040* |
| ECAP 100 μg/ml | 0.706 ± 0.060** |

Values are means ± SD (n = 3).
P < 0.01 as compared with the control group.
*P < 0.05 as compared with the vehicle group.
**P < 0.01 as compared with the vehicle group.

The results in Table 2, Table 4, Table 5 and FIGS. 1 and 2 show that ECAP can inhibit the activation of macrophages induced by lipopolysaccharide to reduce the gene and protein expression of inducible nitric oxide synthase of macrophages, and thereby, reduce the production of nitric oxide.

The results of Experiments A to C indicate that ECAP can inhibit the activation of macrophages, and thus, it can inhibit the inflammatory reaction of macrophages.

Example 2

Inhibition Test of Mouse Chronic Hepatitis Induced by $CCl_4$

Experiment D

Induction of Mouse Chronic Hepatitis

Thirty-six ICR (Institute of Cancer Research) mice were divided into four groups, wherein one group was as a control group, and the mice in the other three groups were administrated with carbon tetrachloride ($CCl_4$) to induce liver damage and liver fibrosis. Carbon tetrachloride (10%) (dissolved in olive oil, 0.1 ml/10 g) were orally administrated to the mice twice a week for 8 weeks. In addition, the mice treated with $CCl_4$ in the three groups were also orally administrated with 0.5 wt % carboxylmethyl cellulose (CMC) or ECAP (100, 200 mg/kg) respectively once a day for 8 weeks. After the administration procedure was finished, the mice were anesthetized by $CO_2$, and the blood was collected from the abdominal vena for determining the biochemical parameters in the plasma. Then, the livers of the mice were quickly dissected out and washed with an ice-cold physiological salt solution. The liver was divided into four parts and separately soaked in 10% by volume of neutral formaldehyde for pathological section, and dried at 100° C. and stored at −80° C.

Experiment E

Determination of the Activity of Alanine Aminotransferase and Aspartate Aminotransferase The blood collected in Experiment D was centrifuged at 4,700 rpm for 15 minutes, and the activity of alanine aminotransferase (ALT) and aspartate aminotransferase (AST) was determined by using an automatic biochemistry instrument (Cobas Mira; Roche, Rotkreuz, Switzerland) and a commercial reagent (Roche Diagnostics, Mannheim, Germany). Plasma ALT and AST are indicators of hepatitis. The result is shown in Table 6.

TABLE 6

| Group | dosage (mg/kg) | ALT (U/L) | AST (U/L) |
|---|---|---|---|
| Control | | 34.8 ± 7.7 | 57.2 ± 8.9 |
| $CCl_4$ + CMC | — | 1488.0 ± 339.3### | 1230.0 ± 143.0### |
| $CCl_4$ + ECAP | 100 | 1007.1 ± 391.5* | 883.7 ± 168.9** |
| | 200 | 790.3 ± 308.9** | 825.4 ± 252.6** |

Values are means ± SD (n = 8).
P < 0.001 as compared with the control group.
*P < 0.05 and
**P < 0.01 as compared with the $CCl_4$ + CMC group.

As shown in Table 6, ECAP can inhibit the increase of plasma ALT and AST activity of the mice induced by $CCl_4$, and this result indicates that ECAP can alleviate hepatitis of the mice induced by $CCl_4$.

Experiment F

Determination of the Level of Liver Fibrosis—Histological Staining

Figure 3:
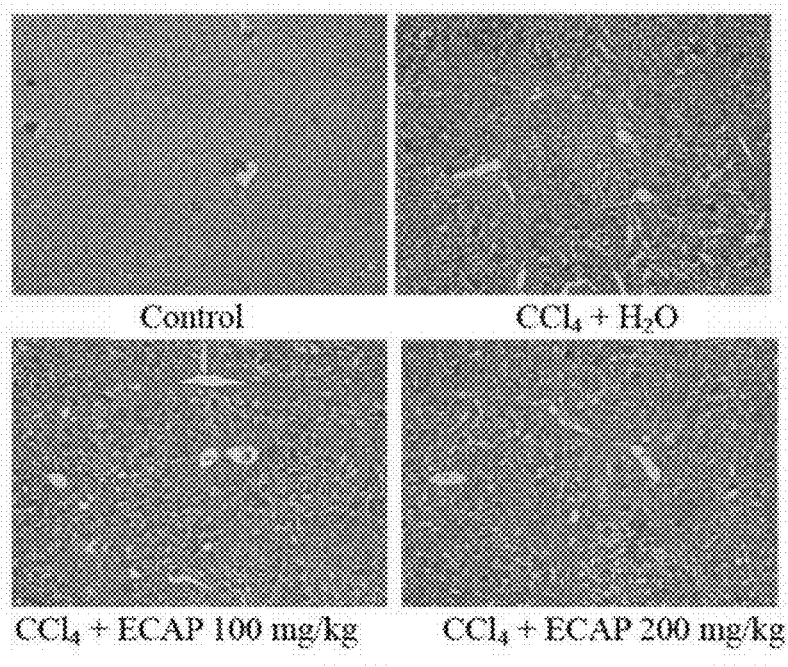
FIG. 3 is an H&E staining picture showing mouse hepatitis induced by $CCl_4$.
Figure 4:
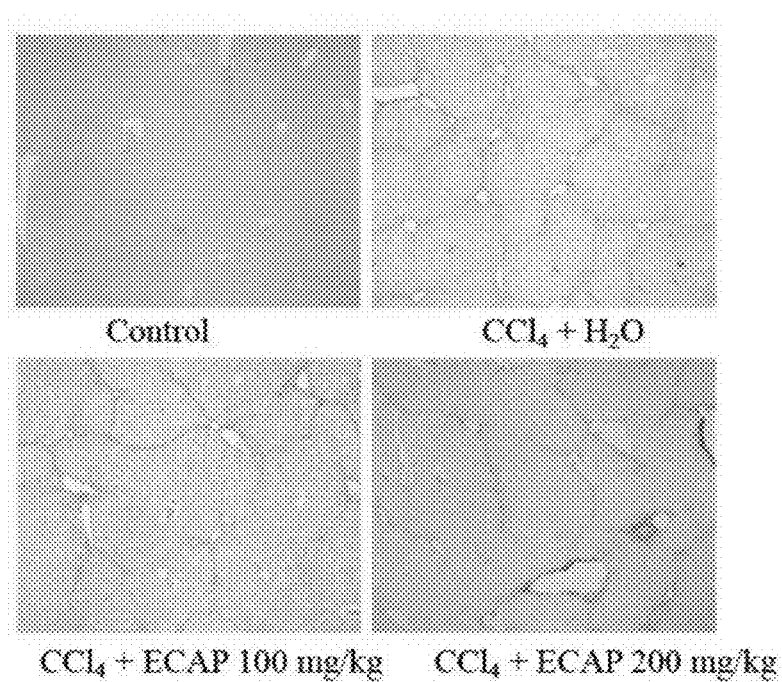
FIG. 4 is a Sirius Red staining picture showing mouse hepatitis induced by $CCl_4$.

The liver tissue obtained in Experiment D was fixed with formaldehyde, embedded with paraffin, sectioned, and stained by hematoxylin and eosin (H&E) stain. As shown in FIG. 3, ECAP can alleviate the severe necrosis of liver cells caused by $CCl_4$.

All kinds of chronic hepatitis and liver damage result in liver fibrosis. The major cause of liver fibrosis is the increase of collagen in extracellular matrix. Thus, the level of liver fibrosis can be evaluated by determining the content of collagen in the liver. Therefore, the following experiment was carried out by using a specific stain for collagen, i.e., Sirius Red stain, and using an image analysis system (Image-Pro Plus version 5.1; Media Cybernetics, MD, USA) to analyze the ratio of liver fibrosis. The results are shown in Table 4 and FIG. 7.

TABLE 7

| Group | Dosage (mg/kg) | Area of fibrosis (%) |
|---|---|---|
| control | — | 1.4 ± 0.3 |
| $CCl_4 + H_2O$ | — | 6.3 ± 2.2### |
| $CCl_4 + ECAP$ | 100 | 3.3 ± 1.2** |
|  | 200 | 3.1 ± 1.4*** |

Values are means ± SD (n = 8).
$p < 0.001$ as compared with the control group.
**$P < 0.01$,
***$P < 0.001$ as compared with the $CCl_4 + H_2O$ group.

Figure 7:
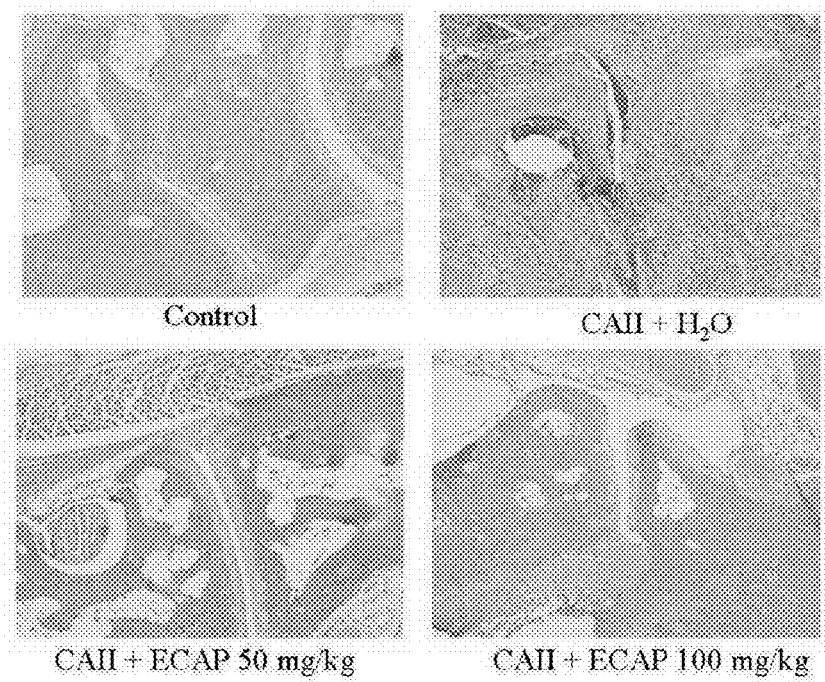
FIG. 7 is an H&E staining picture showing the inhibition of ECAP on mouse arthritis induced by collagen type II.

Table 4 and FIG. 7 indicate that ECAP can decrease the level of liver fibrosis.

Experiment G

Determination of the Level of Liver Fibrosis-Analysis of Collagen

Because hydroxyproline is a special amino acid in collagen, the level of liver fibrosis can be evaluated from the content of hydroxyproline in the liver. The method for determining the content of hydroxyproline in the liver tissue was based on Neuman R E., Logan M A. The determination of hydroxyproline. *J. Biol. Chem.* 1950; 184:299-306, which is entirely incorporated hereinto by reference. After the dried liver tissue was hydrolyzed, $H_2O_2$ was added to the tissue to conduct an oxidation reaction. Then, p-dime hylaminobenzoaldehyde was used for color presenting, and the absorbance was determined under a wavelength of 540 nm. The result is shown in Table 8.

TABLE 8

| Group | Dosage (mg/kg) | hydroxyproline (μg/g-tissue) |
|---|---|---|
| contol | — | 226.2 ± 66.5 |
| $CCl_4 + CMC$ | — | 421.8 ± 93.3### |
| $CCl_4 + ECAP$ | 100 | 365.5 ± 129.4* |
|  | 200 | 316.4 ± 54.8** |

Values are means ± SD (n = 8).
$P < 0.001$ as compared with the control group.
*$P < 0.05$,
**$P < 0.01$ and
***$P < 0.001$ as compared with the $CCl_4 + CMC$ group.

The result in Table 8 indicates that ECAP can decrease the content of hydroxyproline in the liver increased by the treatment of $CCl_4$, illustrating that ECAP can alleviate liver fibrosis.

Experiment H

Determination of the Activation of Liver Kupffer Cells-Immunostaining

Hepatitis induced by $CCl_4$ can activate macrophages in the liver (i.e., Kupffer cells) by the production of lipopolysaccharide, making macrophages produce cytokines and cause liver damage. Lipopolysaccharide can react with CD14 on Kupffer cells and activate the inflammatory reaction of Kupffer cells (which can be seen in Su, G, L., 2002. Lipopolysaccharides in liver injury: molecular mechanisms of Kupffer cell activation. *Am. J. Physiol.* 283, G256-G265, which is entirely incorporated hereinto by reference). Therefore, the immunostaining for CD14 was carried out to determine if ECAP can alleviate liver fibrosis by inhibiting the activation of Kupffer cells from the expression of CD14.

In this experiment, the pathological sections were de-waxed and dehydrated by ethanol, and the endogenous peroxidase was removed by adding 3% by volume of $H_2O_2$ to the sections. Five percent by volume of milk was added thereto and incubated for 30 minutes to block the non-specific binding. Then, a CD14 antibody was added into the sections and incubated at room temperature for 2 hours. The sections were washed by phosphate buffered saline (PBS). Next, a secondary antibody was added into the sections and incubated at room temperature for 30 minutes. An immunodetection kit and diaminobenzidine were used for color presenting, and the sections were stained by hematoxylin, and were sealed after dehydration.

Figure 5:
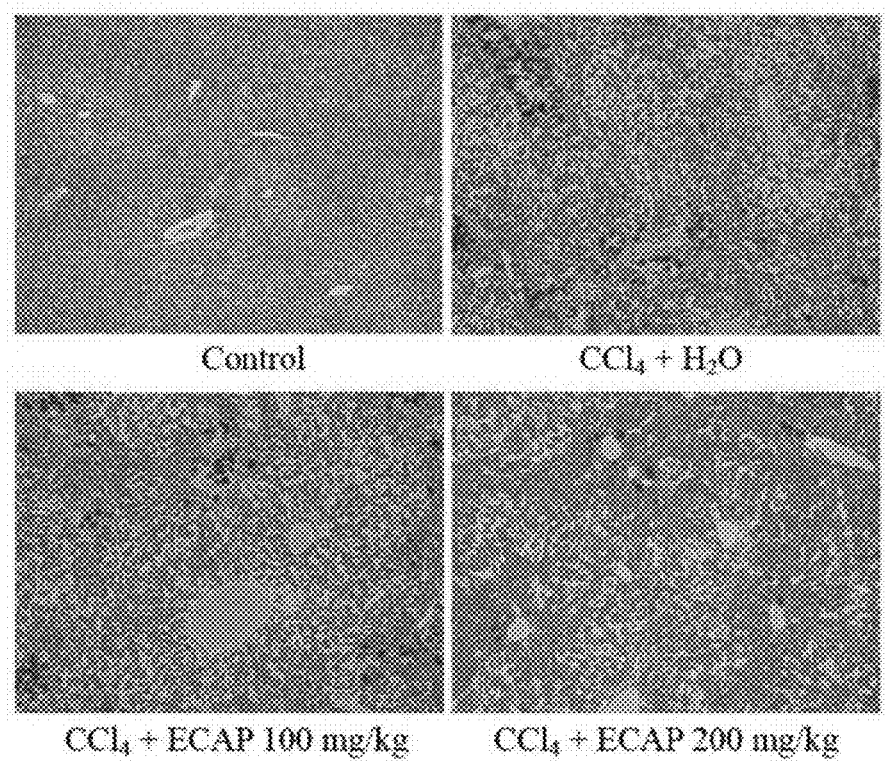
FIG. 5 is an immunostaining picture of CD14 showing mouse hepatitis induced by $CCl_4$.

As shown in FIG. 5, ECAP can decrease the expression of CD14, illustrating that ECAP can alleviate liver fibrosis by inhibiting the activation of Kupffer cells.

Example 3

Inhibition Test of Mouse Arthritis Induced by Collagen Type II

Experiment I

Evaluation of the Symptom of Arthritis

Rheumatoid arthritis is a kind of chronic inflammation of a joint cavity. Long-term inflammation in a joint cavity may stimulate macrophages to differentiate into osteoclasts. Osteoclasts can produce matrix metalloproteinase-9 (MMP-9) to decompose the bone matrix and cause bone damage. In addition, matrix metalloproteinase-9 also relates to the proliferation, migration and/or invasion of tumor cells.

DBA/1J male mice (The Jackson Laboratory, Bar Harbor, Me., USA) weighted 25 g were used in this experiment. The mice were raised in an animal room at constant temperature (21-24° C.) under an illumination cycle of 12-hours of light (illumination time: from 8 a.m. to 8 p.m.), and were fed with standard mice feedstuff. The mice were randomly divided into four groups, six mice in each group, wherein one group was a control group, and the other three groups were arthritis model groups (CIA groups), in which mouse arthritis was induced by collagen type II (CII). CII was dissolved in a 50 mM acetic acid solution, and the solution was placed in a refrigerator under 4° C. overnight to completely dissolve CII; the CII concentration in the solution was 2 mg/ml. Then, 100 μl of the CII solution was emulsified by adding 100 complete freund's adjuvant (CFA) thereinto. After the emulsification was finished, the emulsified solution was subcutaneously injected into the tails of the mice (100 μg/mouse). After 21 days, the CII solution was emulsified by mixing with an equivalent amount of incomplete freund's adjuvant (IFA). After the emulsification was finished, the emulsified solution was subcutaneously injected into the tails of the mice (100 μg/mouse). The sensitized CIA mice in the three groups were divided into an $H_2O$ control group (fed with 10 ml/kg of water) and ECAP groups (administrated with 50 or 100 mg/kg of ECAP). The mice were further injected with CII again, and the next day, the mice were administrated with ECAP continuously for 20 days. On the $21^{st}$ day, the CIA mice were sacrificed, and the blood, kidneys, groin lymph nodes, and two back ankles of the mice were removed and collected for the following analysis.

After the mice were sensitized, the joints in the limbs of the mice were observed once per five days to evaluate the level of inflammation and swelling and other variation according to Thorbecke's method (which can be seen in Thorbecke et al., Modulation by cytokines of induction of oral tolerance to type II collagen. *Arthritis Rheum.*, 1999, 42(1): 110-8, which is entirely incorporated hereinto by reference). The following five symptoms were used as the basis for evaluation and grading.

Figure 6A:
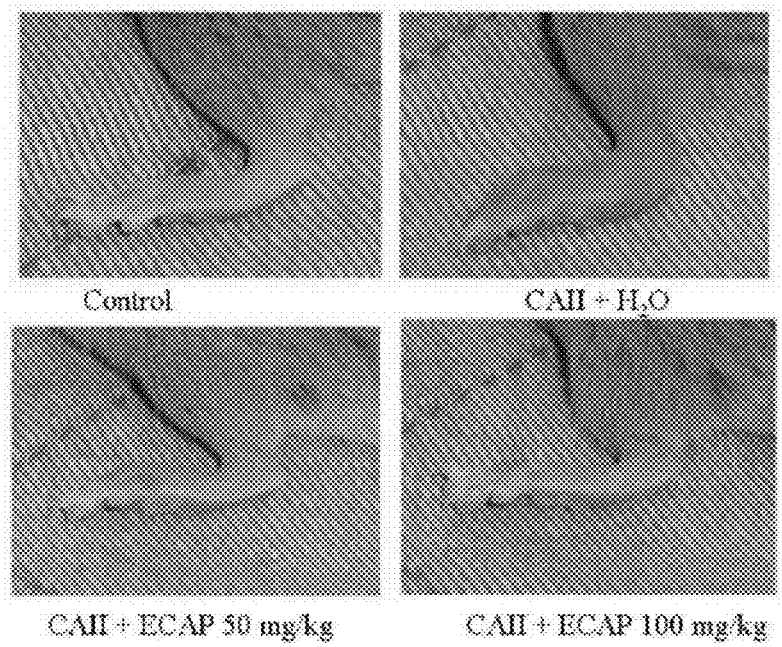
FIGS. 6A and 6B are respectively a picture and an evaluation curve diagram showing the inhibition of ECAP on mouse arthritis induced by collagen type II.
Figure 6B:
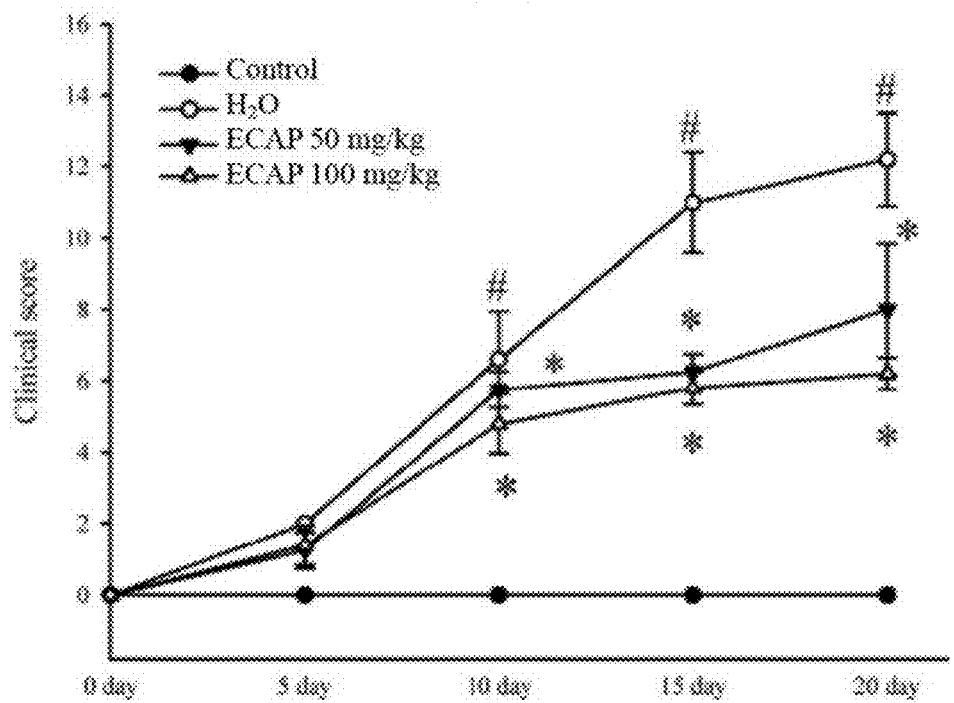

0: no symptom of arthritis
1: reddish and slightly swollen thenar and tarsus
2: moderately reddish swollen tarsus and ankle
3: severe reddish swollen tarsus and ankle
4: stiff joint and distortional bone The results are shown in FIGS. 6A and 6B.

Experiment J

Analysis of Pathological Section

After the CIA mice in Experiment I were sacrificed, the tissue from the right thenar to tibia was removed and fixed in 10% by volume of formaldehyde. Next day, the muscle and pelt on the thenar were removed, and the thenar was soaked in 10% by volume of fresh formaldehyde for a week. Then, the thenar was soaked in 15 wt % ethylenediamine tetra-acetic acid (EDTA) for decalcification. The decalcification solution was replaced once per two days. Two weeks later, the thenar was embedded with paraffin and sectioned. The section was stained by hematoxylin and eosin stain. The result is shown in FIG. 7.

Figure 8:
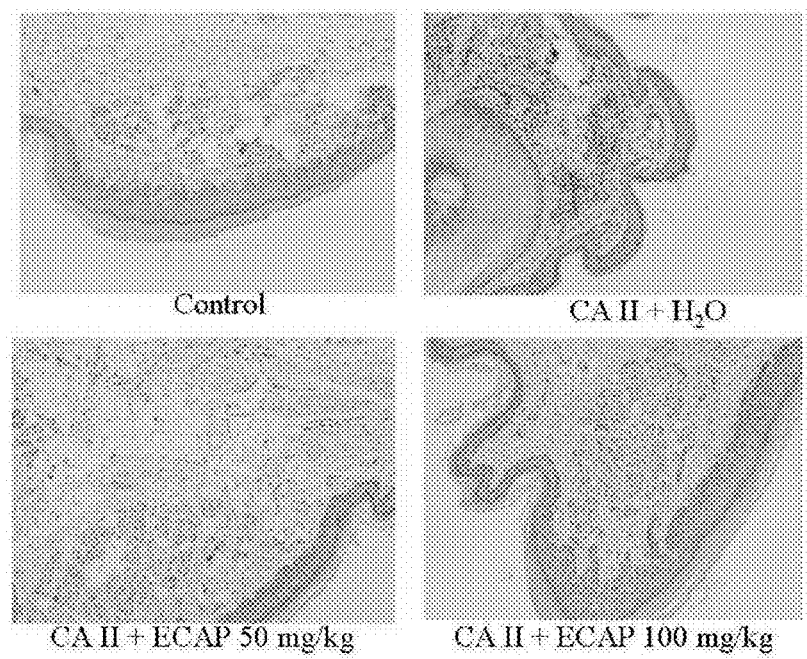
FIG. 8 is an immunohistochemical staining picture showing the inhibition of ECAP on the expression of matrix metalloproteinase-9 resulting from mouse arthritis induced by collagen type II.

Then, immunohistochemical staining was carried out by using anti-rabbit MMP-9 (Millipore, Mass., USA) and a 3,3'-diaminobenzidine immunodetection kit (Sigma-Aldrich, St. Louis, Mo., USA) for color presenting. The section was observed by an optical microscope. The result is shown in FIG. 8.

Experiment K

RT-PCR Analysis of Thenar Tissue

Figure 9A:
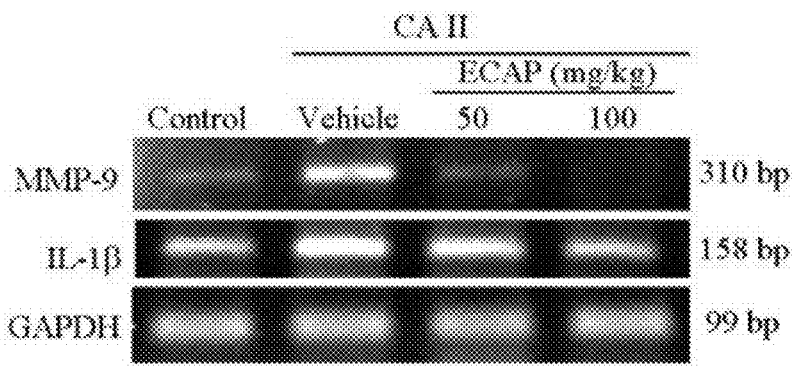
FIGS. 9A to 9C are respectively an electrophoresis picture and statistic column diagrams showing the inhibition of ECAP on the mRNA expression of matrix metalloproteinase-9 and IL-1β resulting from mouse arthritis induced by collagen type II.
Figure 9B:
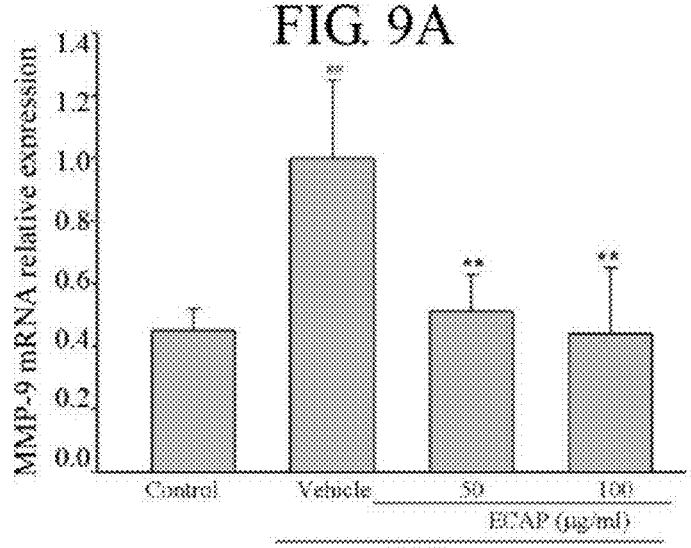
Figure 9C:
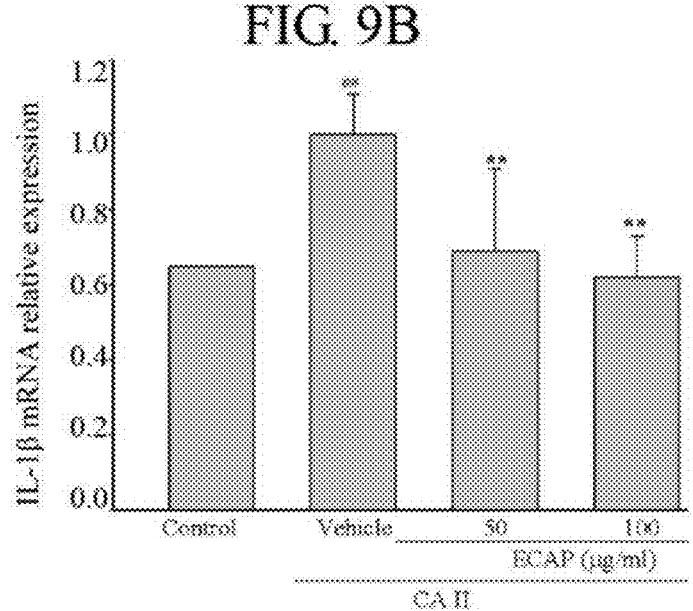

The thenars of the mice were frozen by liquid nitrogen and ground, and the RNAs were extracted therefrom and reverse transcribed into cDNAs. The mRNA content of cytokine IL-1β (Interleukin-1β) and matrix metalloproteinase-9 was analyzed by RT-PCR. The primers used in this experiment are shown in Table 9. The results are shown in FIGS. 9A to 9C and Table 10.

TABLE 9

| gene | primer sequence | length (b.p.) | cycles | Tm (° C.) |
|---|---|---|---|---|
| IL-1β | R: TGGTTTCTCTTCCCAAGACC (SEQ ID NO. 5) F: TTCAAGGGGACATTAGGCAG (SEQ ID NO. 6) R: TGTGCTGGTGCTTCATTCAT (SEQ ID NO. 7) R: AGGGACAGAACCTGCCTGG (SEQ ID NO. 8) | 158 | 35 | 51 |
| MMP-9 | F: GGTCTAGGCCCAGAGGTA (SEQ ID NO. 9) R: GGTCGTAGGTCACGTAGC (SEQ ID NO. 10) | 310 | 35 | 57 |
| GAPDH | F: CTTCATTGACCTCAACTACATGGTC TA (SEQ ID NO. 3) R: GATGACAAGCTTCCCATTCTC AG (SEQ ID NO. 4) | 99 | 35 | 55 |

TABLE 10

| Group | IL-1β mRNA relative expression | MMP-9 mRNA relative expression |
|---|---|---|
| control | 0.65 ± 0.00 | 0.45 ± 0.07 |
| H₂O | 1.00 ± 0.11## | 1.00 ± 0.25## |
| ECAP 50 mg/kg | 0.62 ± 0.11** | 0.51 ± 0.12** |
| ECAP 100 mg/kg | 0.69 ± 0.22* | 0.44 ± 0.21** |

Values are means ± SD (n = 3).
$P < 0.01$ as compared with the control group.
*$P < 0.05$ as compared with the H₂O group.
**$P < 0.01$ as compared with the H₂O group.

The results in Experiments I to K (FIGS. 6A to 9C and Table 10) indicate that ECAP can effectively inhibit arthritis of the DBA/1J mice induced by collagen type II. In addition to inhibiting inflammation, ECAP can also decrease the bone damage. In addition, ECAP can inhibit the gene expression of matrix metalloproteinase-9 and IL-1β. Matrix metalloproteinase-9 has the effect of decomposing the bone matrix, which is the major cause of bone damage resulting from arthritis. The mechanism of the inhibition effect of ECAP on the expression of matrix metalloproteinase-9 was studied in the following cell model experiments.

Example 4

Inhibition Test of the Expression of MMP-9 in Macrophages Stimulated by RANKL

Experiment L

RT-PCR Analysis

ECAP with different concentrations (0, 10, 25, and 50 μg/ml) was added into a culture dish (comprising α-MEM (α-minimum essential medium), 10 wt % heat inactivated FBS, 1 wt % PSA (comprising penicillin, streptomycin, amphotericin)) comprising RAW 264.7 macrophages. After 1 hour, 50 ng/ml RANKL (receptor for activation of nuclear factor kappa B ligand) was added into the culture dish. After being cultured for 24 hours, the cells were collected, and the RNAs thereof were extracted, and RT-PCR analysis was conducted. The primers used in this experiment were identical to the primers shown in Table 9 of Example 3.

Figure 10:
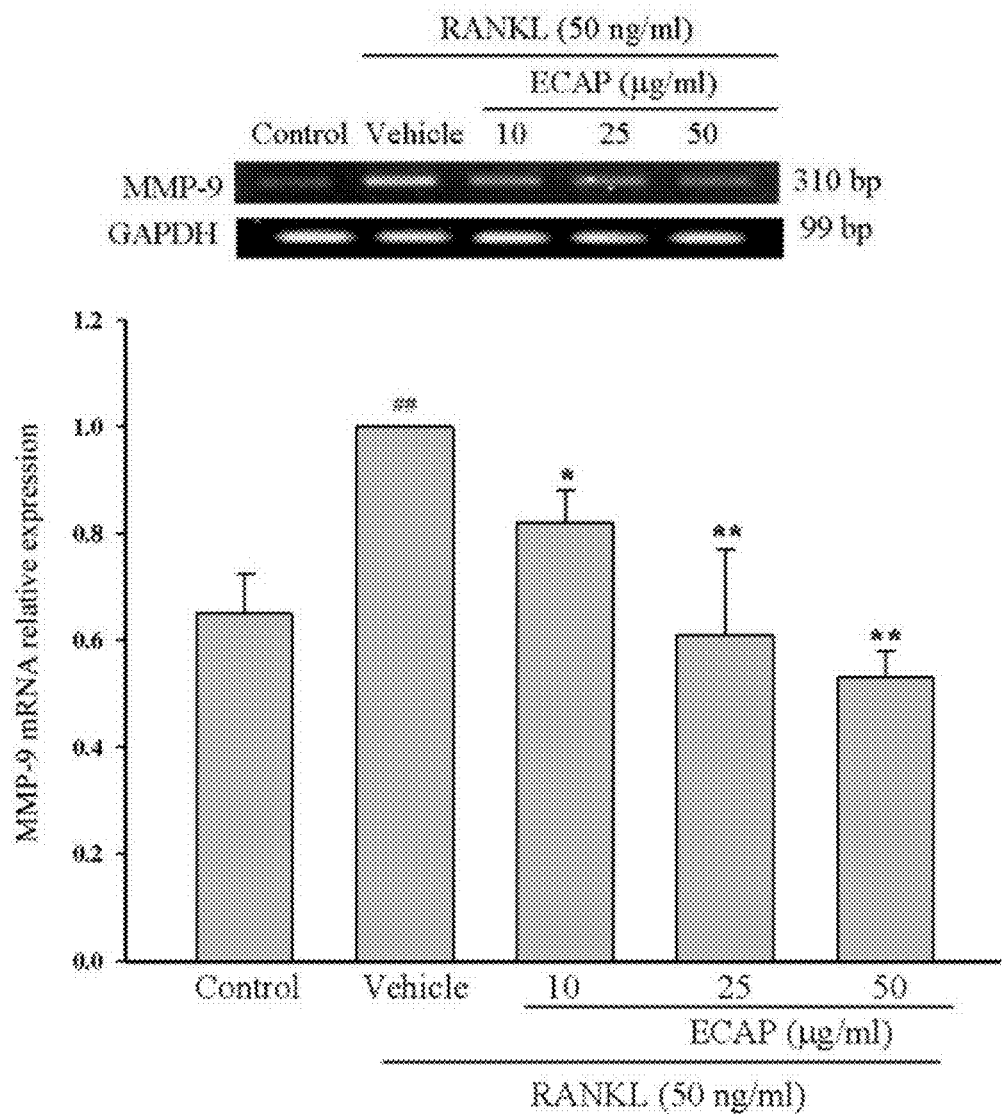
FIG. 10 is an electrophoresis picture and a statistic column diagram showing the inhibition of ECAP on the gene expression of matrix metalloproteinase-9 in macrophages stimulated by RANKL.

The results are shown in FIG. 10 and Table 11.

TABLE 11

| Group | MMP-9 mRNA relative expression |
|---|---|
| control | 0.65 ± 0.07 |
| H₂O | 1.00 ± 0.00## |
| ECAP 10 μg/ml | 0.82 ± 0.06 |
| ECAP 25 μg/ml | 0.61 ± 0.16** |
| ECAP 50 μg/ml | 0.53 ± 0.05** |

Values are means ± SD (n = 3).
$P < 0.01$ as compared with the control group.
**$P < 0.01$ as compared with H₂O group.

Experiment M

Zymography Assay

Figure 11:
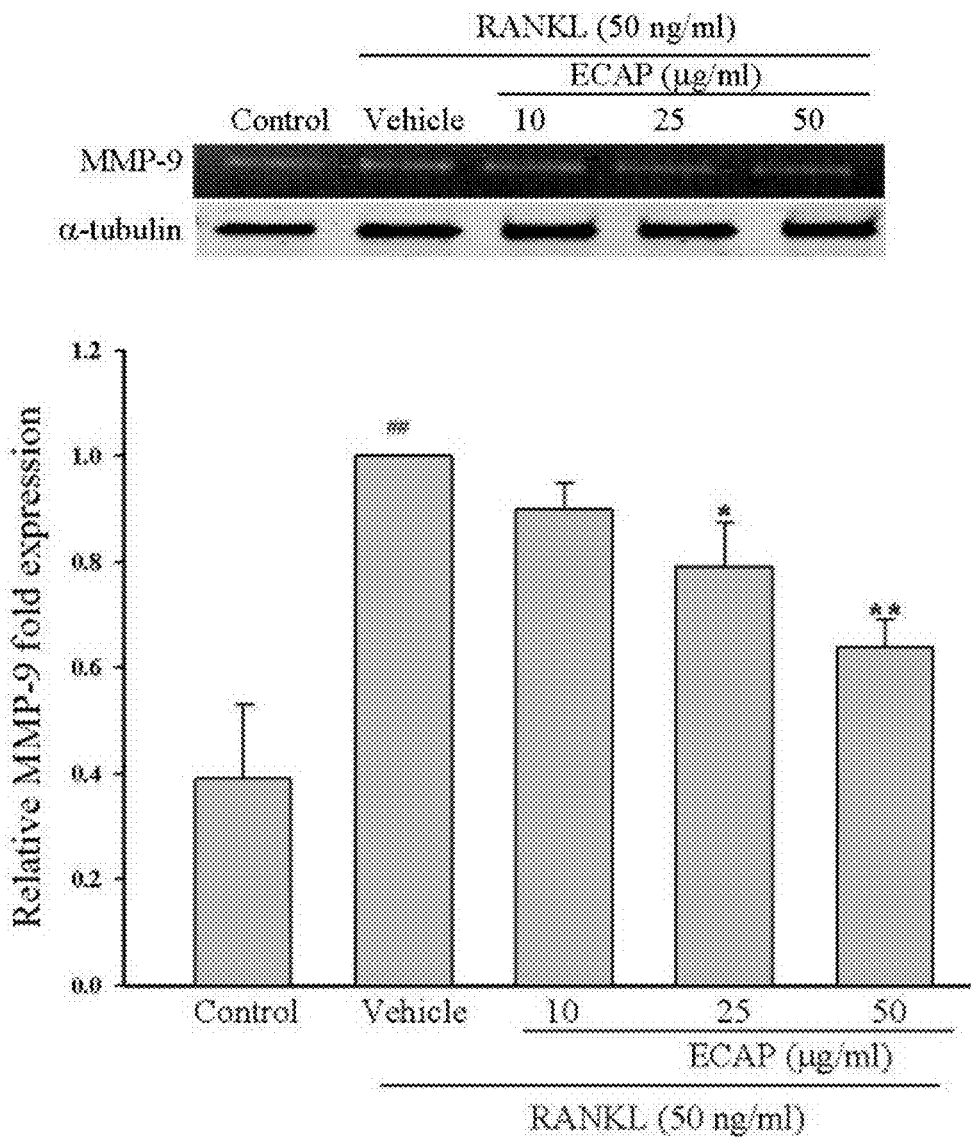
FIG. 11 is an electrophoresis picture and a statistic column diagram showing the inhibition of ECAP on the protein expression of matrix metalloproteinase-9 in macrophages stimulated by RANKL.

Because matrix metalloproteinase-9 is capable of decomposing gelatin, the content of matrix metalloproteinase-9 can be determined by a zymography assay. First, the culture solution of the cells in above Experiment L was collected and centrifuged at 1000×g under 4° C. for 10 minutes. The supernatant was collected for conducting a zymography assay. A four-fold loading dye was added into 30 µg of the culture solution and incubated for 10 minutes, and the sample was analyzed by electrophoresis with 10% by volume of SDS-PAGE, wherein the resolving gel comprised 0.1% by volume of gelatin. Then, the electrophoresis gel was soaked with a rinsing buffer solution (3% by volume of Triton X-100) for 30 minutes twice, and a developing buffer solution (containing 50 mM Tris base, 40 mM HCl, 200 mM NaCl, 5 mM $CaCl_2$, and 0.2 w/v % $NaN_3$) was added to the gel and shaken for 30 minutes. Then, the gel was washed, and a fresh developing buffer solution was added to the gel again, which was incubated at 37° C. for 16 hours. Finally, the gel was stained with Coomassie blue (containing 0.2 w/v % Coomassie blue R-250, 50% by volume of methanol and 10% by volume of acetic acid) for 30 minutes, and destained by a destaining solution (containing 10% by volume of acetic acid and 30% by volume of methanol); the destaining solution was replaced every 15 minutes. After destaining was finished, the gel was soaked in a gel drying solution (containing 50% by volume of deionized water, 50% by volume of methanol, and 0.33% by volume of glycerol) for 30 minutes, and was made into a dried gel by cellophane paper and an acrylic sheet for observation. The results are shown in FIG. 11 and Table 12.

TABLE 12

| Group | MMP-9 relative expression fold |
|---|---|
| control | 0.39 ± 0.14 |
| $H_2O$ | 1.00 ± 0.00[##] |
| ECAP 10 µg/ml | 0.90 ± 0.05 |
| ECAP 25 µg/ml | 0.79 ± 0.08* |
| ECAP 50 µg/ml | 0.64 ± 0.05** |

Values are means ± SD (n = 3).
[##]$P < 0.01$ as compared with the control group.
*$P < 0.05$,
**$P < 0.01$ as compared with the $H_2O$ group.

Experiment N

Luciferase Assay

Raw 264.7 macrophages were cultured in a 24-well culture dish overnight ($5×10^4$ cells/well), and a pGL3.0-MMP-9 promoter was transfected into the cells. After 16 hours, ECAP (10, 25, 50 mg/ml) was added to the cells, and the cells were stimulated by RANKL (50 ng/ml) for 24 hours, and the expression of the reporter gene was determined. The method comprised the following steps:

(1) Preparation of Plasmid DNA

DH5α *E. coli* strains with a recombinant plasmid were cultured in an LB broth (comprising 50 µg/ml ampicillin) overnight, and the plasmid DNA was extracted by a Midi kit (Qiagen, Valencia, Calif., USA). The method is summarized as follows: the culture broth was centrifuged at 6,000×g under 4° C. for 30 minutes, the supernatant was discarded, and the bacteria were evenly mixed with 4.5 ml buffer S1. Then, 4.5 ml buffer S2 was added into the sample and gently shaken 4 to 6 times, and the sample was placed under room temperature for 5 minutes. Next, 4.5 ml buffer S3K was added into the sample and evenly mixed at once, and the sample was placed under room temperature for 5 minutes. Then, 4.5 ml buffer B was added into the sample and gently shaken 4 to 6 times, and the sample was centrifuged at 5000×g under 4° C. for 30 minutes. The supernatant obtained from the previous step was passed through a Midiprep syringe filter by gravity to remove the impurities and the clear filtrate was passed through a Midiprep column by gravity. The column was eluted with 7 ml buffer W1, followed by 8 ml buffer W2. The bottom Midiprep column was taken out and placed in a 2-ml eppendorf tube, and the tube was centrifuged at 12000×g under 4° C. for 2 minutes. The remaining buffer W2 was discarded, and the plasmid DNA was eluted by a preheated (65° C.) elution buffer. The absorbance of the sample was measured by a spectrophotometer under wavelengths of 260 nm and 280 nm to determine the concentration and purity of the DNA sample. The DNA sample was stored at −80° C.

(2) Transfection

Raw 264.7 macrophages were cultured in a 24-well culture dish overnight ($5×10^4$ cells/well). The next day, the plasmid DNA (0.5 µg) was mixed with an FBS-free culture broth (200 µl) and spun down. Then, the broth was mixed with 1 µl jetPRIME™, spun down, and placed under room temperature for 10 minutes. The broth containing the plasmid DNA (0.5 µg) was mixed with 0.4 µg pNF-κB-Luc and 0.1 µg of a pRL-TKY vector. The macrophages were washed with an FBS-free culture broth twice, and 200 µl of an FBS-free culture broth was added into each well. Then, 200 µl of the above premixed culture broth containing the plasmid DNA/jetPRIME™ was added into each well. After 4 hours, a culture broth (comprising 20 wt % FBS and 2 wt % PSA) was added into each well. The next day, the cells were washed with PBS twice, and 1 ml of a fresh culture broth was added into the cells. Then, the pNF-κB-Luc transfected cells were pretreated with ECAP for 1 hour, and treated with RANKL (50 ng/ml) for 24 hours.

(3) Detection of the Expression of the Reporter Gene

Figure 12:
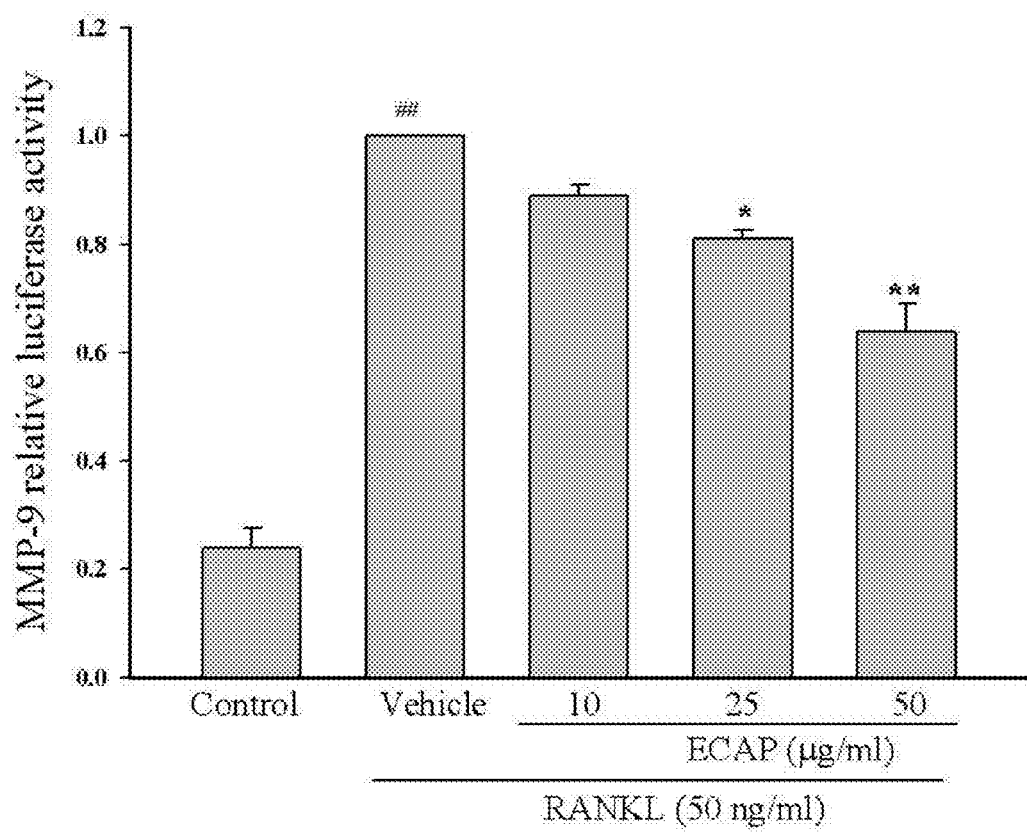
FIG. 12 is a statistic column diagram showing the inhibition of ECAP on the protein expression of matrix metalloproteinase-9 in macrophages stimulated by RANKL.

After the above reaction was finished, the cells were washed with ice-cold PBS twice, and 100 µl of a passive lysis buffer (Promega, Madison, Wis., USA) was added into the cells. Then, the cells were collected from the dish and transferred into a centrifuge tube, frozen and thawed between −80° C. and room temperature repeatedly for 3 times, and centrifuged at 12,000×g under 4° C. for 1 minute, and the supernatant was collected. The activity of firefly luciferase and renilla luciferase (as an indicator of transfection efficiency) was determined by a Dual-Luciferase reporter assay kit (Promega, Madison, Wis., USA). The testing steps of this assay were as follows. The supernatant (50 µl) obtained from the previous step was translocated into a tube. The tube was placed in a luminometer (TD-20/20 Luminometer), and the background value was measured for 5 seconds, and 100 µl of a luciferase assay reagent II was added into the tube and evenly mixed. Bioluminescence was continuously recorded for 10 seconds. Then, 100 µl of a Stop and Glo reagent was added therein and evenly mixed, and bioluminescence was recorded for 10 seconds. The results are shown in FIG. 12 and Table 13.

TABLE 13

| Group | MMP-9 relative luciferase activity |
|---|---|
| control | 0.24 ± 0.03 |
| $H_2O$ | 1.00 ± 0.00[##] |
| ECAP 10 µg/ml | 0.89 ± 0.02 |
| ECAP 25 µg/ml | 0.81 ± 0.02* |
| ECAP 50 µg/ml | 0.64 ± 0.05** |

Values are means ± SD (n = 3).
[##]$P < 0.01$ as compared with the control group.
*$P < 0.05$,
**$P < 0.01$ as compared with the $H_2O$ group.

The results in Experiments L to N (FIGS. 10 to 12 and Tables 11 to 13) indicate that ECAP has the effect of inhibiting the gene and protein expression of matrix metalloproteinase-9 of macrophages stimulated by RANKL.

Example 5

Inhibition Test of MMP-9 Expression via NF-κB Pathway

Experiment O

Electrophoretic Mobility Shift Assay

NF-κB (nuclear factor-κB) is a nuclear factor regulating the transcription of various genes. In general, NF-Kb is present in cytoplasm and binds to IκB protein (inhibitory protein of NF-κB) in the dimmer form of p65/p50. When being stimulated, IκB will be phosphorylated by IκB kinase. The phosphorylated IκB (p-IκB) will be degraded to activate NF-κB, which will then translocate into the nucleus to participate in gene transcription, and influence the expression of transcription regulation proteins, such as NFATc1 (Nuclear factor of activated T-cells, cytoplasmic 1), and thereby, influence the expression of matrix metalloproteinase-9.

Electrophoretic Mobility Shift Assay (EMSA) was carried out to determine if ECAP could inhibit the expression of matrix metalloproteinase-9 by decreasing the amount of NF-κB translocating into the nucleus of macrophages.

In this experiment, ECAP with different concentrations (0, 10, 25, and 50 μg/ml) was added into a culture dish comprising RAW 264.7 macrophages. After being cultured for 1 hour, the cells were treated with RANKL (50 ng/ml) and cultured for 60 minutes. Proteins within the nucleus were extracted and analyzed by EMSA. The DNA sequences used in this experiment are as follows:

```
                                             (SEQ ID NO. 11)
cy5-5'-TCGACCAACTGGGGACTCTCCCTTTGGGAACA-3'

(SEQ ID NO. 12)
cy5-5'-TCGATGTTCCCAAAGGGAGAGTCCCCAGTTGG-3'.
```

Figure 13A:
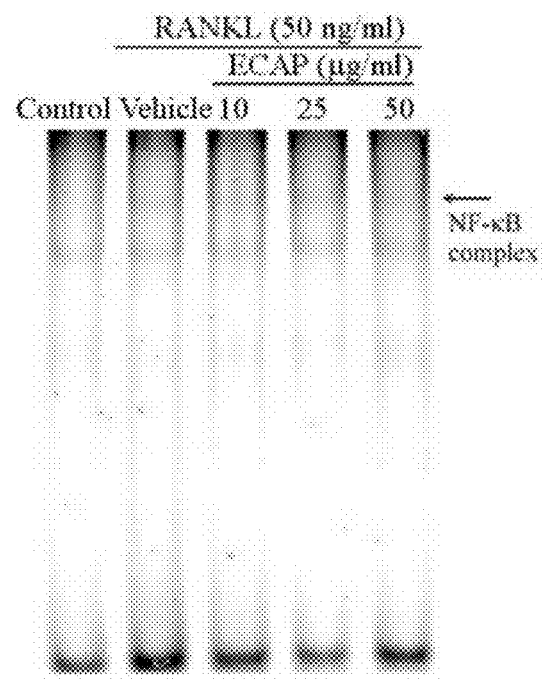
FIGS. 13A and 13B are respectively an EMSA electrophoresis picture and a statistic column diagram showing the inhibition of ECAP on intranuclear NF-κB protein in macrophages stimulated by RANKL.
Figure 13B:
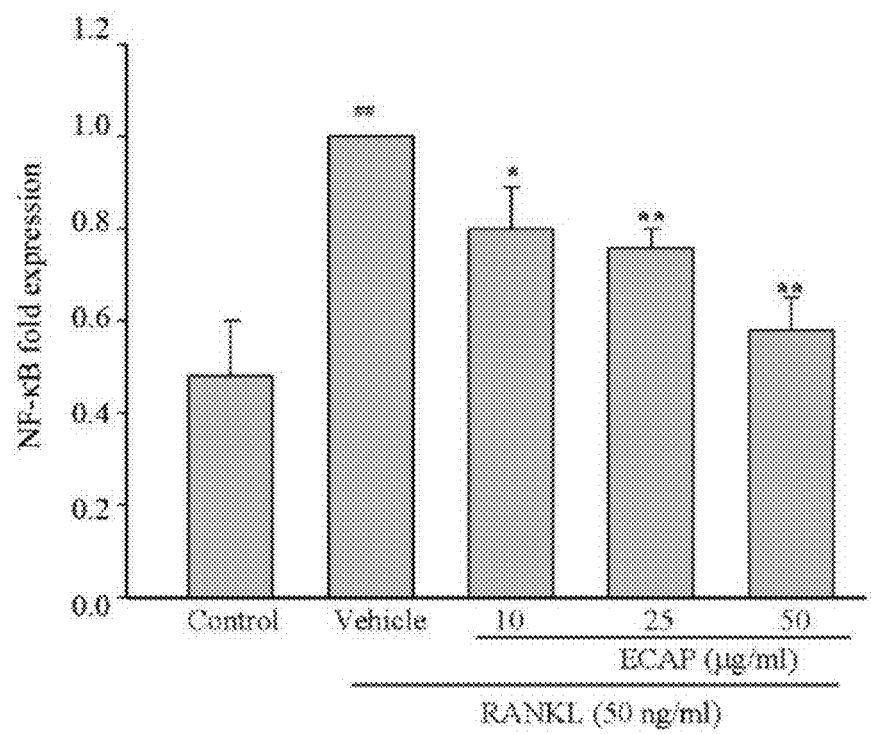

The results are shown in FIGS. 13A and 13B and Table 14.

TABLE 14

| Group | NF-κB relative expression |
|---|---|
| control | 0.48 ± 0.12 |
| vehicle | 1.00 ± 0.00## |
| ECAP 10 μg/ml | 0.80 ± 0.09* |

TABLE 14-continued

| Group | NF-κB relative expression |
|---|---|
| ECAP 25 μg/ml | 0.76 ± 0.04** |
| ECAP 50 μg/ml | 0.58 ± 0.07** |

Values are means ± SD (n = 3).
$P < 0.01$ as compared with the control group.
*$P < 0.05$,
**$P < 0.01$ as compared with the vehicle group.

The results in FIGS. 13A and 13B and Table 14 indicate that ECAP can inhibit the translocation of NF-κB in the macrophages stimulated by RANKL.

Experiment P

Western Blot Analysis

Figure 14:
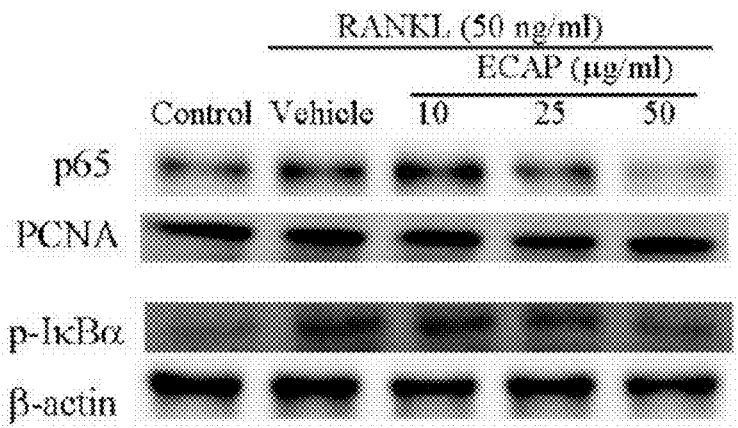
FIG. 14 is an electrophoresis picture showing the inhibition of ECAP on the protein expression of p65 and p-IκBα in macrophages stimulated by RANKL.
Figure 15:
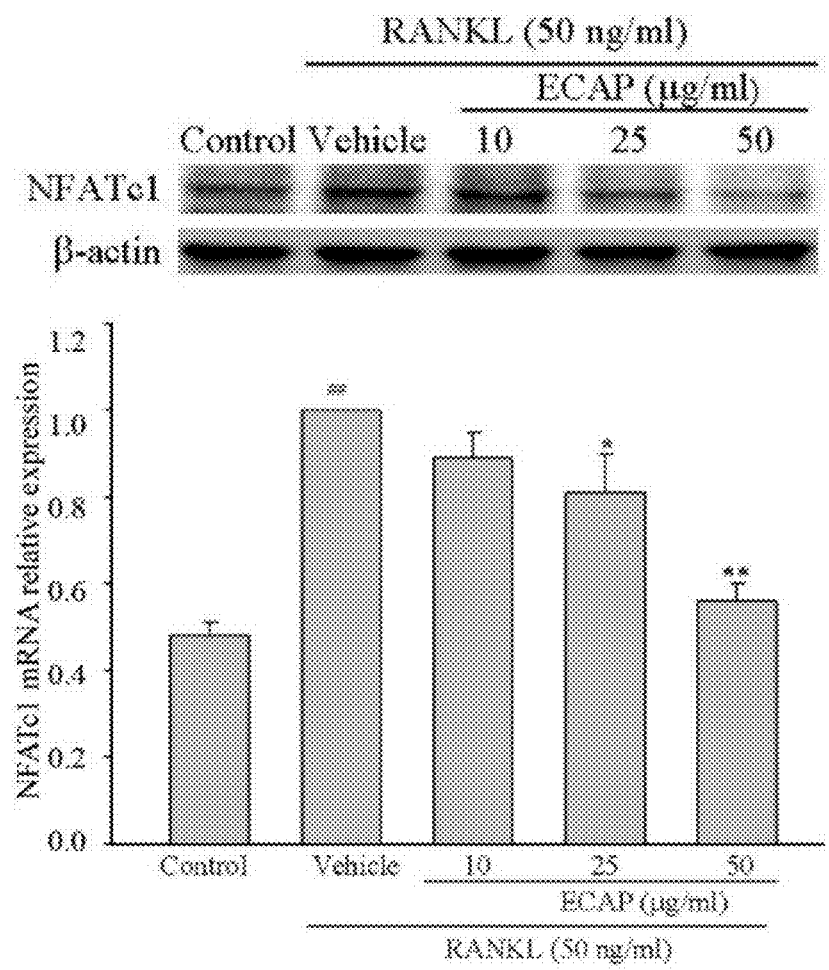
FIG. 15 is a protein electrophoresis picture and an mRNA statistic column diagram showing the inhibition of ECAP on the expression of NFATc-1 in macrophages stimulated by RANKL.

This experiment was carried out by adding a differentiation reagent, RANKL (50 ng/ml), into a culture dish comprising RAW 264.7 macrophages, and then ECAP with different concentrations (0, 10, 25, and 50 μg/ml) was added thereto. After the RAW 264.7 macrophages were cultured for 60 minutes, proteins in the nucleus and cytoplasm were extracted, and the protein expression of p65 in the nucleus and p-IκBα in the cytoplasm was analyzed independently by Western Blot. In addition, the total proteins within the cells were extracted, and the expression of NFATc1 protein was analyzed by Western Blot. The results are shown in FIGS. 14 and 15 and Table 15.

TABLE 15

| Group | MMP-9 relative expression |
|---|---|
| control | 0.48 ± 0.03 |
| $H_2O$ | 1.00 ± 0.00## |
| ECAP 10 μg/ml | 0.89 ± 0.09 |
| ECAP 25 μg/ml | 0.81 ± 0.03* |
| ECAP 50 μg/ml | 0.56 ± 0.04** |

Values are means ± SD (n = 3).
$P < 0.05$ as compared with the control group.
*$P < 0.05$,
**$P < 0.01$ as compared with the $H_2O$ group.

The results in FIGS. 14 and 15 and Table 15 indicate that ECAP can inhibit the protein expression of p65 and p-IκBα and decrease the amount of NF-κB translocating into the nucleus, thereby, decreasing the protein expression of matrix metalloproteinase-9. Therefore, ECAP can inhibit the expression of matrix metalloproteinase-9 by decreasing the amount of NF-κB translocating into the nucleus of macrophages.

Examples 3 to 5 indicate that ECAP can inhibit the expression of matrix metalloproteinase-9, and thus, it can be used for curing the diseases related to matrix metalloproteinase-9, such as inhibiting the proliferation, migration and/or invasion of tumor cells.

What is claimed is:

1. A method for inhibiting the activation of macrophages in a subject, comprising administering to the subject in need thereof, an effective amount of an active component selected from the group consisting of a compound of formula (I), a pharmaceutically acceptable salt of the compound, and combinations thereof:

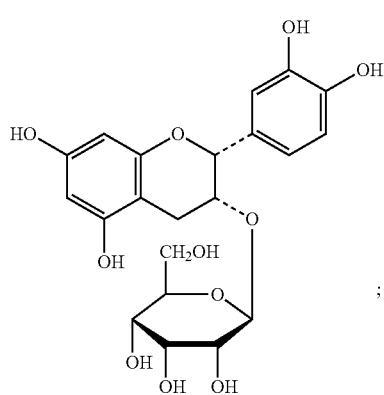

and wherein the dosage of said administering is selected to effectively treat arthritis or hepatitis.

2. The method as claimed in claim 1, wherein the subject has rheumatoid arthritis.

3. The method as claimed in claim 1, further comprising: wherein the active component is administered as a pharmaceutical composition.

4. The method as claimed in claim 1, wherein the active component is administered by oral administration, subcutaneous injection, intravenous injection, or intra-articular injection.

5. The method as claimed in claim 1, wherein the active component is the compound of formula (I).

6. A method for treating inflammation in a subject, comprising administering to the subject in need thereof, an effective amount of an active component selected from the group consisting of a compound of formula (I), a pharmaceutically acceptable salt of the compound, and combinations thereof:

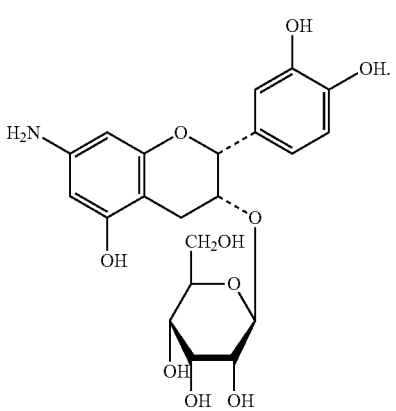

7. The method as claimed in claim 6, further comprising: wherein the active component is administered as a pharmaceutical composition.

8. The method as claimed in claim 6, wherein the active component is administered by oral administration, subcutaneous injection, intravenous injection, or intra-articular injection.

9. The method as claimed in claim 6, wherein the active component is the compound of formula (I).

* * * * *